United States Patent
Kong et al.

(10) Patent No.: US 10,293,159 B2
(45) Date of Patent: May 21, 2019

(54) MEASURING THE "ON-SKIN" TIME OF A TRANSCUTANEOUS ELECTRICAL NERVE STIMULATOR (TENS) DEVICE IN ORDER TO MINIMIZE SKIN IRRITATION DUE TO EXCESSIVE UNINTERRUPTED WEARING OF THE SAME

(71) Applicant: NeuroMetrix, Inc., Waltham, MA (US)

(72) Inventors: Xuan Kong, Acton, MA (US); Shai N. Gozani, Brookline, MA (US)

(73) Assignee: NeuroMetrix, Inc., Waltham, MA (US)

( * ) Notice: Subject to any disclaimer, the term of this patent is extended or adjusted under 35 U.S.C. 154(b) by 0 days.

(21) Appl. No.: 15/621,382

(22) Filed: Jun. 13, 2017

(65) Prior Publication Data
US 2017/0368345 A1   Dec. 28, 2017

Related U.S. Application Data (63) Continuation of application No. 14/794,588, filed on Jul. 8, 2015, now Pat. No. 9,675,801, which is a
(Continued)

(51) Int. Cl.
*A61N 1/04* (2006.01)
*A61N 1/32* (2006.01)
*A61N 1/36* (2006.01)

(52) U.S. Cl.
CPC ....... *A61N 1/36021* (2013.01); *A61N 1/0456* (2013.01); *A61N 1/0476* (2013.01);
(Continued)

(58) Field of Classification Search
CPC .............. A61N 1/36021; A61N 1/0456; A61N 1/36014; A61N 1/0492; A61N 1/0476; A61N 1/321
See application file for complete search history.

(56) References Cited

U.S. PATENT DOCUMENTS

| 1,741,962 A | 12/1929 | Theodoropulos |
|---|---|---|
| D263,869 S | 4/1982 | Sumiyasu |

(Continued)

FOREIGN PATENT DOCUMENTS

| CN | 1919139 | 2/2007 |
|---|---|---|
| CN | 101626804 | 1/2010 |

(Continued)

OTHER PUBLICATIONS

Ancoli-Israel, S. et al., The Role of Actigraphy in the Study of Sleep and Circadian Rhythms, Sleep, 2003, 26(3), p. 342-392.
(Continued)

*Primary Examiner* — Catherine M Voorhees
(74) *Attorney, Agent, or Firm* — Pandiscio & Pandiscio (57) ABSTRACT

Apparatus for providing transcutaneous electrical nerve stimulation (TENS) therapy to a user, the apparatus comprising: a stimulation unit for electrically stimulating at least one nerve of the user; an electrode array connectable to the stimulation unit, the electrode array comprising a plurality of electrodes for electrical stimulation of the at least one nerve of the user; a monitoring unit electrically connected to the stimulation unit for monitoring the on-skin status of the electrode array; an analysis unit for analyzing the on-skin status of the electrode array to determine the effective on-skin time of the electrode array; and a feedback unit for alerting the user when the analysis unit determine that the effective on-skin time exceeds a threshold.

31 Claims, 9 Drawing Sheets

Related U.S. Application Data continuation-in-part of application No. 14/610,757, filed on Jan. 30, 2015, now Pat. No. 9,656,070, which is a continuation of application No. 13/678,221, filed on Nov. 15, 2012, now Pat. No. 8,948,876, said application No. 14/794,588 is a continuation-in-part of application No. 14/269,887, filed on May 5, 2014, now Pat. No. 9,827,420, which is a continuation-in-part of application No. 14/230,648, filed on Mar. 31, 2014, now Pat. No. 9,474,898, and a continuation-in-part of application No. 14/253,628, filed on Apr. 15, 2014.

(60) Provisional application No. 61/560,029, filed on Nov. 15, 2011, provisional application No. 61/657,382, filed on Jun. 8, 2012, provisional application No. 61/806,481, filed on Mar. 29, 2013, provisional application No. 61/811,864, filed on Apr. 15, 2013, provisional application No. 61/819,159, filed on May 3, 2013, provisional application No. 61/858,150, filed on Jul. 25, 2013, provisional application No. 62/021,807, filed on Jul. 8, 2014.

(52) U.S. Cl.
CPC ........... *A61N 1/0492* (2013.01); *A61N 1/321* (2013.01); *A61N 1/36014* (2013.01)

(56) References Cited

U.S. PATENT DOCUMENTS

| | | | |
|---|---|---|---|
| 4,503,863 A | 3/1985 | Katims | |
| 4,605,010 A | 8/1986 | McEwen | |
| 4,738,250 A | 4/1988 | Fulkerson et al. | |
| 5,063,929 A | 11/1991 | Bartelt et al. | |
| 5,121,747 A | 6/1992 | Andrews | |
| 5,169,384 A | 12/1992 | Bosniak et al. | |
| D346,029 S | 4/1994 | Shalvi | |
| 5,350,414 A | 9/1994 | Kolen | |
| 5,429,589 A | 7/1995 | Cartmell et al. | |
| 5,479,939 A | 1/1996 | Ogino | |
| 5,487,759 A | 1/1996 | Bastyr et al. | |
| 5,562,718 A | 10/1996 | Palermo | |
| 5,806,522 A | 9/1998 | Katims | |
| D411,887 S | 7/1999 | Agarwala | |
| 5,948,000 A | 9/1999 | Larsen et al. | |
| 6,099,488 A | 8/2000 | Hung | |
| 6,161,044 A | 12/2000 | Silverstone | |
| 6,266,558 B1 | 7/2001 | Gozani et al. | |
| D450,313 S | 11/2001 | Koinuma | |
| 6,430,450 B1 | 8/2002 | Bach-y-Rita et al. | |
| D462,772 S | 9/2002 | Lamping et al. | |
| 6,456,884 B1 | 9/2002 | Kenney | |
| 6,662,051 B1 | 12/2003 | Eraker et al. | |
| D541,042 S | 4/2007 | Andre et al. | |
| D566,383 S | 4/2008 | Harris et al. | |
| D592,200 S | 5/2009 | Liu | |
| D598,556 S | 8/2009 | Chen | |
| D607,198 S | 1/2010 | Andre et al. | |
| 7,668,598 B2 | 2/2010 | Herregraven et al. | |
| D611,611 S | 3/2010 | Sachi et al. | |
| D615,526 S | 5/2010 | Andre et al. | |
| 7,720,548 B2 | 5/2010 | King | |
| 7,725,193 B1 | 5/2010 | Chu | |
| 7,787,946 B2 | 8/2010 | Stahmann et al. | |
| D625,829 S | 10/2010 | Arbesman et al. | |
| D629,115 S | 12/2010 | Robertson | |
| D636,881 S | 4/2011 | Clemens et al. | |
| D637,988 S | 5/2011 | Jinkinson | |
| 8,108,049 B2 | 1/2012 | King | |
| 8,121,702 B2 | 2/2012 | King | |
| 8,131,374 B2 | 3/2012 | Moore et al. | |
| D658,302 S | 4/2012 | Nixon | |
| D680,735 S | 4/2013 | Itabashi et al. | |
| 8,421,642 B1 | 4/2013 | McIntosh et al. | |
| D688,707 S | 8/2013 | Vincent et al. | |
| D705,428 S | 5/2014 | Cheney et al. | |
| D712,045 S | 8/2014 | Thornton | |
| 8,825,175 B2 | 9/2014 | King | |
| 8,862,238 B2 | 10/2014 | Rahimi et al. | |
| D716,963 S | 11/2014 | Yosef et al. | |
| 8,948,876 B2 | 2/2015 | Gozani et al. | |
| D732,682 S | 6/2015 | Porat | |
| 9,168,375 B2 | 10/2015 | Rahimi et al. | |
| D744,661 S | 12/2015 | Rizzi | |
| D750,263 S | 2/2016 | Shigeno et al. | |
| D750,798 S | 3/2016 | Yosef et al. | |
| D754,973 S | 5/2016 | Danze et al. | |
| D757,292 S | 5/2016 | Chen | |
| D758,605 S | 6/2016 | Chen | |
| D758,606 S | 6/2016 | Chen | |
| D759,262 S | 6/2016 | Chen | |
| D759,263 S | 6/2016 | Chen | |
| D759,958 S | 6/2016 | Requa | |
| D762,628 S | 8/2016 | Yoon et al. | |
| D762,872 S | 8/2016 | Chen | |
| D767,775 S | 9/2016 | Gilmer et al. | |
| 9,452,287 B2 | 9/2016 | Rosenbluth et al. | |
| 9,474,898 B2 | 10/2016 | Gozani et al. | |
| D774,654 S | 12/2016 | Anderson | |
| D778,453 S | 2/2017 | Knaus et al. | |
| D779,677 S | 2/2017 | Chen | |
| 9,561,397 B2 | 2/2017 | Zaki | |
| D784,544 S | 4/2017 | Dudkiewicz et al. | |
| D784,546 S | 4/2017 | Gordon | |
| D784,946 S | 4/2017 | Jun et al. | |
| D788,056 S | 5/2017 | Choi et al. | |
| 9,656,070 B2 | 5/2017 | Gozani et al. | |
| D789,546 S | 6/2017 | Matfus et al. | |
| D789,547 S | 6/2017 | Matfus et al. | |
| D791,333 S | 7/2017 | Wilson | |
| D792,363 S | 7/2017 | Kim et al. | |
| D794,331 S | 8/2017 | Grote | |
| 9,731,126 B2 | 8/2017 | Ferree et al. | |
| D801,542 S | 10/2017 | Anderson | |
| D802,780 S | 11/2017 | Hsu | |
| D806,669 S | 1/2018 | Kangasmaa et al. | |
| D810,843 S | 2/2018 | Karvandi | |
| D811,729 S | 3/2018 | Byshhe | |
| D813,407 S | 3/2018 | Chen | |
| D813,408 S | 3/2018 | Chen | |
| D828,569 S | 9/2018 | Mercuro | |
| D829,182 S | 9/2018 | Li | |
| D830,565 S | 10/2018 | Xu | |
| D831,017 S | 10/2018 | Choe et al. | |
| D831,221 S | 10/2018 | Smith | |
| D831,335 S | 10/2018 | Crease | |
| D832,230 S | 10/2018 | Lee et al. | |
| 2002/0010497 A1 | 1/2002 | Merfeld et al. | |
| 2003/0023192 A1 | 1/2003 | Foxlin | |
| 2003/0074037 A1* | 4/2003 | Moore | A61N 1/36021 607/63 |
| 2003/0114892 A1 | 6/2003 | Nathan et al. | |
| 2003/0208246 A1 | 11/2003 | Kotlik et al. | |
| 2004/0122483 A1 | 6/2004 | Nathan et al. | |
| 2005/0059903 A1 | 3/2005 | Izumi | |
| 2005/0080463 A1 | 4/2005 | Slahmann et al. | |
| 2006/0052788 A1 | 3/2006 | Thelen et al. | |
| 2006/0085049 A1 | 4/2006 | Cory et al. | |
| 2006/0095088 A1 | 5/2006 | De Ridder | |
| 2006/0173507 A1 | 8/2006 | Mrva et al. | |
| 2006/0190057 A1 | 8/2006 | Reese | |
| 2007/0060922 A1 | 3/2007 | Dreyfuss | |
| 2007/0276449 A1 | 11/2007 | Gunter et al. | |
| 2008/0077192 A1 | 3/2008 | Harry et al. | |
| 2008/0146980 A1 | 6/2008 | Rousso et al. | |
| 2008/0147143 A1 | 6/2008 | Popovic et al. | |
| 2008/0147146 A1 | 6/2008 | Wahlgren et al. | |
| 2008/0312709 A1 | 12/2008 | Volpe et al. | |
| 2009/0030476 A1 | 1/2009 | Hargrove | |
| 2009/0112214 A1 | 4/2009 | Philippon et al. | |
| 2009/0131993 A1 | 5/2009 | Rousso et al. | |

(56) References Cited

U.S. PATENT DOCUMENTS

| | | |
|---|---|---|
| 2009/0240303 A1 | 9/2009 | Wahlstrand et al. |
| 2009/0264789 A1 | 10/2009 | Molnar et al. |
| 2009/0270947 A1 | 10/2009 | Stone et al. |
| 2009/0326604 A1* | 12/2009 | Tyler .................... A61B 5/0492 607/45 |
| 2010/0004715 A1 | 1/2010 | Fahey |
| 2010/0042180 A1 | 2/2010 | Mueller et al. |
| 2010/0057149 A1 | 3/2010 | Fahey |
| 2010/0087903 A1 | 4/2010 | Van Herk et al. |
| 2010/0094103 A1 | 4/2010 | Kaplan et al. |
| 2010/0114257 A1 | 5/2010 | Torgerson |
| 2010/0131028 A1* | 5/2010 | Hsu ...................... A61B 5/4815 607/42 |
| 2010/0198124 A1 | 8/2010 | Bhugra |
| 2010/0217349 A1 | 8/2010 | Fahey |
| 2010/0241464 A1 | 9/2010 | Amigo et al. |
| 2011/0066209 A1 | 3/2011 | Bodlaender et al. |
| 2011/0224665 A1 | 9/2011 | Crosby et al. |
| 2011/0257468 A1 | 10/2011 | Oser et al. |
| 2011/0264171 A1 | 10/2011 | Torgerson |
| 2011/0276107 A1* | 11/2011 | Simon ................ A61N 1/36021 607/46 |
| 2011/0282164 A1 | 11/2011 | Yang et al. |
| 2012/0010680 A1 | 1/2012 | Wei et al. |
| 2012/0108998 A1 | 5/2012 | Molnar et al. |
| 2013/0096641 A1 | 4/2013 | Strother et al. |
| 2013/0158627 A1 | 6/2013 | Gozani et al. |
| 2013/0217998 A1 | 8/2013 | Mahfouz et al. |
| 2014/0039450 A1 | 2/2014 | Green et al. |
| 2014/0057232 A1 | 2/2014 | Wetmore et al. |
| 2014/0081353 A1* | 3/2014 | Cook ................... A61N 1/0456 607/59 |
| 2014/0107729 A1* | 4/2014 | Sumners ............ A61N 1/36003 607/48 |
| 2014/0163444 A1 | 6/2014 | Ingvarsson et al. |
| 2014/0245791 A1 | 9/2014 | Proud et al. |
| 2014/0276549 A1* | 9/2014 | Osorio ................ A61M 5/1723 604/503 |
| 2014/0296934 A1 | 10/2014 | Gozani et al. |
| 2014/0296935 A1 | 10/2014 | Ferree et al. |
| 2014/0309709 A1* | 10/2014 | Gozani .............. A61N 1/36021 607/46 |
| 2014/0336730 A1 | 11/2014 | Simon et al. |
| 2014/0379045 A1 | 12/2014 | Rahimi et al. |
| 2015/0045853 A1 | 2/2015 | Alataris et al. |
| 2015/0174402 A1 | 6/2015 | Thomas et al. |
| 2015/0321000 A1* | 11/2015 | Rosenbluth .......... A61N 1/0492 607/48 |
| 2015/0328467 A1 | 11/2015 | Demers et al. |
| 2015/0335288 A1 | 11/2015 | Toth et al. |
| 2016/0367823 A1 | 12/2016 | Cowan et al. |

FOREIGN PATENT DOCUMENTS

| | | |
|---|---|---|
| CN | 102355847 | 2/2012 |
| CN | 102740919 | 10/2012 |
| DE | 102010052710 | 5/2012 |
| JP | 61-171943 | 10/1986 |
| JP | 4-347140 | 12/1992 |
| JP | 9-117453 | 5/1997 |
| JP | 2000-167067 | 6/2000 |
| JP | 2005-34402 | 2/2005 |
| JP | 2006-68300 | 3/2006 |
| JP | 4185846 | 9/2008 |
| WO | WO 97/42999 | 11/1997 |
| WO | WO 99/64105 | 12/1999 |
| WO | WO 2003/051453 | 6/2003 |
| WO | WO 2004/078132 | 9/2004 |
| WO | WO 2007/061746 | 5/2007 |
| WO | WO 2008/079757 | 7/2008 |
| WO | WO 2008/088985 | 7/2008 |
| WO | WO 2011/075179 | 6/2011 |
| WO | WO 2011/137193 | 11/2011 |
| WO | WO 2012/116407 | 9/2012 |

OTHER PUBLICATIONS

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.

Bloodworth DM et al., Comparison of stochastic vs. conventional transcutaneous electrical stimulation for pain modulation in patients with electromyographically documented radiculopathy. American Journal of Physical Medicine & Rehabilitation, 2004, vol. 83(8): 584-591.

Chandran P et al., Development of opioid tolerance with repeated transcutaneous electrical nerve stimulation administration, Pain, 2003, vol. 102: 195-201.

Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.

Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.

Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.

Chen CC et al., Does the pulse frequency of transcutaneous electrical nerve stimulation (TENS) influence hypoalgesia? A systematic review of studies using experimental pain and healthy human participants, Physiotherapy, 2008, vol. 94: 11-20.

Claydon LS et al., Dose-specific effects of transcutaneous electrical nerve stimulation on experimental pain, Clinical Journal of Pain, 2011, vol. 27(7): 635-647.

Cole, R.J. et al., Automatic Sleep/Wake Identification From Wrist Activity, Sleep, 1992, 15(5), p. 461-469.

Cruccu G. et al., EFNS guidelines on neurostimulation therapy for neuropathic pain, European Journal of Neurology, 2007, vol. 14: 952-970.

Davies HTO et al., Diminishing returns or appropriate treatment strategy?—an analysis of short-term outcomes after pain clinic treatment, Pain, 1997, vol. 70: 203-208.

Desantana JM et al., Effectiveness of transcutaneous electrical nerve stimulation for treatment of hyperalgesia and pain, Curr Rheumatol Rep. 2008, vol. 10(6): 492-499.

Dubinsky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.

Fary RE et al., Monophasic electrical stimulation produces high rates of adverse skin reactions in healthy subjects, Physiotherapy Theory and Practice, 2011, vol. 27(3): 246-251.

Fishbain, David A. et al. Does Pain Mediate the Pain Interference with Sleep Problem in Chronic Pain? Findings from Studies for Management of Diabetic Peripheral Neuropathic Pain with Duloxetine, Journal of Pain Symptom Management, Dec. 2008;36(6):639-647.

Fishbain, David A. et al., Transcutaneous Electrical Nerve Stimulation (TENS) Treatment Outcome in Long-Term Users, The Clinical Journal of Pain, Sep. 1996;12(3).201-214.

Food and Drug Administration, Draft Guidance for Industry and Staff: Class II Special Controls Guidance Document: Transcutaneous Electrical Nerve Stimulator for Pain Relief, Apr. 5, 2010.

Garrison DW et al., Decreased activity of spontaneous and noxiously evoked dorsal horn cells during transcutaneous electrical nerve stimulation (TENS), Pain, 1994, vol. 58: 309-315.

Gilron, I. et al., Chronobiological Characteristics of Neuropathic Pain: Clinical Predictors of Diurnal Pain Rhythmicity, The Clinical Journal of Pain, 2013.

(56) References Cited

OTHER PUBLICATIONS

Hori, T. et al., Skin Potential Activities and Their Regional Differences During Normal Sleep in Humans, The Japanese Journal of Physiology, 1970, vol. 20, p. 657-671.
Jelinek HF et al., Electric pulse frequency and magnitude of perceived sensation during electrocutaneous forearm stimulation, Arch Phys Med Rehabil, 2010, vol. 91: 1372-1382.
Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.
Johnson MI et al., Analgesic effects of different frequencies of transcutaneous electrical nerve stimulation on cold-induced pain in normal subjects, Pain, 1989, vol. 39: 231-236.
Johnson MI et al., Transcutaneous Electrical Nerve Stimulation (TENS) and TENS-like devices: do they provide pain relief?, Pain Reviews, 2001, vol. 8: 7-44.
Johnson MI et al., Transcutaneous electrical nerve stimulation for the management of painful conditions: focus on neuropathic pain, Expert Review of Neurotherapeutics, 2011, vol. 11(5): 735-753.
Johnson, M.I. et al., An in-depth study of long-term users of transcutaneous electrical nerve stimulation (TENS). Implications for clinical use of TENS. Pain. Mar. 1991;44(3):221-229.
Kaczmarek, Kurt A. et al.. Electrotactile and Vibrotactile Displays for Sensory Substitution Systems. IEEE Trans. Biomed. Eng. Jan. 1991;38 (1):1-16.
Kantor G et al., The effects of selected stimulus waveforms on pulse and phase characteristics at sensory and motor thresholds, Physical Therapy, 1994, vol. 74(10): 951-962.
Keller, Thierry et al., Electrodes for transcutaneous (surface) electrical stimulation, J. Automatic Control, University of Belgrade. 2008;18(2):35-45.
Koumans, A. J. R. et al., Electrodermal Levels and Fluctuations During Normal Sleep, Psychophysiology, 1968, 5(3), p. 300-306.
Kripke, D.F. et al., Wrist Actigraphic Scoring for Sleep Laboratory Patients: Algorithm Development, Journal of Sleep Research, 2010, 19(4), p. 612-619.
Law PPW et al., Optimal stimulation frequency of transcutaneous electrical nerve stimulation on people with knee osteoarthritis, J Rehabil Med, 2004, vol. 36: 220-225.
Leonard G et al., Deciphering the role of endogenous opioids in high-frequency TENS using low and high doses of naloxone, Pain, 2010, vol. 151: 215-219.
Levy et al., A comparison of two methods for measuring thermal thresholds in diabetic neuropathy, Journal of Neurology, Neurosurgery, and Psychiatry, 1989, vol. 52: 1072-1077.
Lykken, D.T., Properties of Electrodes Used in Electrodermal Measurement, J. Comp. Physiol. Psychol. Oct. 1959;52:629-634.
Lykken, D.T., Square-Wave Analysis of Skin Impedance. Psychophysiology. Sep. 1970;7(2):262-275.
Melzack R et al., Pain mechanisms: A New Theory, Science, 1965, vol. 150(3699): 971-979.
Moran F et al., Hypoalgesia in response to transcutaneous electrical nerve stimulation (TENS) depends on stimulation intensity, The Journal of Pain, 2011, vol. 12(8): 929-935.
Oosterhof, Jan et al., Outcome of transcutaneous electrical nerve stimulation in chronic pain: short-term results of a double-blind, randomised, placebo-controlled trial. J. Headache Pain. Sep. 2006;7(4):196-205.
Oosterhof, Jan et al., The long-term outcome of transcutaneous electrical nerve stimulation in the treatment for patients with chronic pain: a randomized, placebo-controlled trial. Pain Pract. Sep. 2012;12(7):513-522.
Pantaleao MA et al., Adjusting pulse amplitude during transcutaneous electrical nerve stimulation (TENS) application produces greater hypoalgesia, The Journal of Pain, 2011, vol. 12(5): 581-590.
Paquet, J. et al., Wake Detection Capacity of Actigraphy During Sleep, Sleep, 2007, 30(10), p. 1362-1369.
Pieber K et al., Electrotherapy for the treatment of painful diabetic peripheral neuropathy: a review, Journal of Rehabilitation Medicine, 2010, vol. 42: 289-295.
Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.
Sadeh, A., The Role and Validity of Actigraphy in Sleep Medicine: An Update, Sleep Medicine Reviews, 2011, vol. 15, p. 259-267.
Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6. p. 79-92.
Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.
Tryon, W. W., Issues of Validity in Actigraphic Sleep Assessment, Sleep, 2004, 27(1), p. 158-165.
Tsai, Y. et al., Impact of Subjective Sleep Quality on Glycemic Control in Type 2 Diabetes Mellitus, Family Practice, 2012, vol. 29, p. 30-35.
Van Boxtel, A., Skin resistance during square-wave electrical pulses of 1 to 10 mA. Med. Biol. Eng. Comput. Nov. 1977;15(6):679-687.
Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.
Webster, J. B. et al., An Activity-Based Sleep Monitor System for Ambulatory Use, Sleep, 1982, 5(4), p. 389-399.
Zelman, D. C. et al., Sleep Impairment in Patients With Painful Diabetic Peripheral Neuropathy, The Clinical Journal of Pain, 2006, 22(8), p. 681-685.
Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.
Bonnet, M, et al., Recording and Scoring Leg Movements, Sleep, 1993, vol. 16, No. 8, p. 748-759.
Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2458.
Kovacevic-Ristanovic, R, et al., Nonpharmacologic Treatment of Periodic Leg Movements in Sleep, Arch. Phys. Med. Rehabil., 1991, vol. 72, p. 385-389.
Lopes, L. et al., Restless Legs Syndrome and Quality of Sleep in Type 2 Diabetes, Diabetes Care, 2005, vol. 28, No. 11, p. 2633-2636.
Nightingale, S., The neuropathic pain market. Nature Reviews, 2012, vol. 11, p. 101-102.
Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.
Sheridan et al., Some Factors Influencing the Threshold of the Electrocutaneous Stimulus, Perceptual and Motor Skills, 1966, vol. 22, pp. 647-654.

* cited by examiner

DETERMINATION OF ON-SKIN TIME DURING THERAPY PERIOD

DETERMINATION OF ON-SKIN TIME DURING THERAPY PERIOD
EQUIVALENT CIRCUIT, TENS DEVICE "ON-SKIN"

FIG. 5

DETERMINATION OF ON-SKIN TIME DURING THERAPY PERIOD
EQUIVALENT CIRCUIT, TENS DEVICE "OFF-SKIN"

DETERMINATION OF ON-SKIN TIME DURING NON-THERAPY PERIOD

FIG. 8

DETERMINATION OF ON-SKIN TIME DURING NON-THERAPY PERIOD
EQUIVALENT CIRCUIT, TENS DEVICE "ON-SKIN"

FIG. 9

DETERMINATION OF ON-SKIN TIME DURING NON-THERAPY PERIOD
EQUIVALENT CIRCUIT, TENS DEVICE "OFF-SKIN"

MEASURING THE "ON-SKIN" TIME OF A TRANSCUTANEOUS ELECTRICAL NERVE STIMULATOR (TENS) DEVICE IN ORDER TO MINIMIZE SKIN IRRITATION DUE TO EXCESSIVE UNINTERRUPTED WEARING OF THE SAME

REFERENCE TO PENDING PRIOR PATENT APPLICATIONS

This patent application is a continuation of pending prior U.S. patent application Ser. No. 14/794,588, filed Jul. 8, 2015 by NeuroMetrix, Inc. for MEASURING THE "ON-SKIN" TIME OF A TRANSCUTANEOUS ELECTRICAL NERVE STIMULATOR (TENS) DEVICE IN ORDER TO MINIMIZE SKIN IRRITATION DUE TO EXCESSIVE UNINTERRUPTED WEARING OF THE SAME, which in turn:

(1) is a continuation-in-part of prior U.S. patent application Ser. No. 14/610,757, filed Jan. 30, 2015 by NeuroMetrix, Inc. and Shai N. Gozani et al. for APPARATUS AND METHOD FOR RELIEVING PAIN USING TRANSCUTANEOUS ELECTRICAL NERVE STIMULATION, which patent application in turn:
  (A) is a continuation of prior U.S. patent application Ser. No. 13/678,221, filed Nov. 15, 2012 by NeuroMetrix, Inc. and Shai N. Gozani et al. for APPARATUS AND METHOD FOR RELIEVING PAIN USING TRANSCUTANEOUS ELECTRICAL NERVE STIMULATION, which in turn claims benefit of:
    (i) prior U.S. Provisional Patent Application Ser. No. 61/560,029, filed Nov. 15, 2011 by Shai N. Gozani for SENSUS OPERATING MODEL; and
    (ii) prior U.S. Provisional Patent Application Ser. No. 61/657,382, filed Jun. 8, 2012 by Shai N. Gozani et al. for APPARATUS AND METHOD FOR RELIEVING PAIN USING TRANSCUTANEOUS ELECTRICAL NERVE STIMULATION;
(2) is a continuation-in-part of pending prior U.S. patent application Ser. No. 14/269,887, filed May 5, 2014 by NeuroMetrix, Inc. and Thomas Ferree et al. for TRANSCUTANEOUS ELECTRICAL NERVE STIMULATOR WITH USER GESTURE DETECTOR AND ELECTRODE-SKIN CONTACT DETECTOR, WITH TRANSIENT MOTION DETECTOR FOR INCREASING THE ACCURACY OF THE SAME, which patent application in turn:
  (A) is a continuation-in-part of prior U.S. patent application Ser. No. 14/230,648, filed Mar. 31, 2014 by Neurometrix, Inc. and Shai Gozani et al. for DETECTING CUTANEOUS ELECTRODE PEELING USING ELECTRODE-SKIN IMPEDANCE, which claims benefit of:
    (i) prior U.S. Provisional Patent Application Ser. No. 61/806,481, filed Mar. 29, 2013 by Shai Gozani for DETECTING ELECTRODE PEELING BY RELATIVE CHANGES IN SKIN-ELECTRODE IMPEDANCE;
  (B) is a continuation-in-part of pending prior U.S. patent application Ser. No. 14/253,628, filed Apr. 15, 2014 by Neurometrix, Inc. and Shai Gozani et al. for TRANSCUTANEOUS ELECTRICAL NERVE STIMULATOR WITH AUTOMATIC DETECTION OF USER SLEEP-WAKE STATE, which claims benefit of:
    (i) prior U.S. Provisional Patent Application Ser. No. 61/811,864, filed Apr. 15, 2013 by Shai Gozani for TRANSCUTANEOUS ELECTRICAL NERVE STIMULATOR WITH AUTOMATIC DETECTION OF PATIENT SLEEP-WAKE STATE;
  (C) claims benefit of prior U.S. Provisional Patent Application Ser. No. 61/819,159, filed May 3, 2013 by Neurometrix, Inc. and Thomas Ferree et al. for TAP DETECTOR WITH HIGH SENSITIVITY AND SPECIFICITY FOR A WEARABLE TRANSCUTANEOUS ELECTRICAL NERVE STIMULATOR; and
  (D) claims benefit of prior U.S. Provisional Patent Application Ser. No. 61/858,150, filed Jul. 25, 2013 by Neurometrix, Inc. and Andres Aguirre et al. for MOVEMENT REGULATED TRIP CONDITIONS IN A WEARABLE TRANSCUTANEOUS ELECTRICAL NERVE STIMULATOR; and
(3) claims benefit of prior U.S. Provisional Patent Application Ser. No. 62/021,807, filed Jul. 8, 2014 by Neurometrix, Inc. and Xuan Kong et al. for MEASURING TENS DEVICE ON-SKIN TIME TO PREVENT AND MINIMIZE SKIN IRRITATION.

The thirteen (13) above-identified patent applications are hereby incorporated herein by reference.

FIELD OF THE INVENTION

This invention relates generally to Transcutaneous Electrical Nerve Stimulation (TENS) devices that deliver electrical currents across the intact skin of a user via electrodes so as to provide symptomatic relief of chronic pain, and more particularly to the measurement of the "on-skin" time of the TENS device in order to minimize skin irritation due to excessive uninterrupted wearing of the TENS device and to profile TENS therapy patterns.

BACKGROUND OF THE INVENTION

Transcutaneous Electrical Nerve Stimulation (TENS) devices apply electrical currents to a particular area of the human body in order to suppress pain. The most common form of TENS is commonly referred to as "conventional TENS". In conventional TENS, electrodes are placed on the user's skin within, or adjacent to, or proximal to, the area of pain. An electrical circuit generates stimulation pulses with specified characteristics. One or more pairs of electrodes, placed on the user's skin, transduce the electrical pulses and thereby stimulate underlying nerves in order to relieve pain. TENS electrodes typically utilize hydrogels to create a stable low-impedance electrode-skin interface to facilitate the delivery of electrical current to the user so as to stimulate peripheral sensory nerves. Close contact of the electrode (both gel pads and backing materials) with the skin of the user creates a temporary barrier that limits the covered skin area from being exposed to the air.

Pain relief from TENS stimulation usually begins within 15 minutes of the stimulation onset and may last up to an hour following the completion of the stimulation period (also known as a "therapy session"). Each therapy session typically runs for 30-60 minutes. To maintain pain relief (i.e., hypoalgesia), TENS therapy sessions typically need to be initiated at regular intervals. Newly developed wearable TENS devices such as the QUELL™ system developed by Neurometrix, Inc. of Waltham, Mass., USA provide users with an option to automatically restart therapy sessions at pre-determined time intervals.

The convenience of "wear-and-forget" TENS technology may lead some users to wear the TENS device for an extended period of time without removing the device from the contacted skin area. Covering the skin area with a TENS device for an extended period of time may cause skin irritation for the user. It is therefore important to monitor the "on-skin" time duration of the TENS device and, where the "on-skin" time duration exceeds a limit, to provide the user with feedback and a reminder (prompt) to "air-out" the skin under the device (i.e., by temporarily removing the TENS device from the user's skin).

SUMMARY OF THE INVENTION

The present invention comprises the provision and use of a novel TENS device which consists of a stimulator designed to be placed on a user's upper calf (or other anatomical location) and a pre-configured electrode array designed to provide circumferential stimulation in the area of the user's upper calf (or other anatomical location). A key feature of the present invention is that the TENS device is adapted to measure the on-skin time of the TENS device. When the on-skin time exceeds a threshold value, feedback and a reminder (prompt) are provided to the user as a reminder to remove the TENS device from the covered skin area in order to allow the skin area to "air-out". Regularly airing-out covered skin areas is an effective means to minimize skin irritation, which is the most frequently reported side effect of TENS therapy.

In one preferred form of the present invention, there is provided apparatus for providing transcutaneous electrical nerve stimulation (TENS) therapy to a user, said apparatus comprising:

a stimulation unit for electrically stimulating at least one nerve of the user;

an electrode array connectable to said stimulation unit, said electrode array comprising a plurality of electrodes for electrical stimulation of the at least one nerve of the user;

a monitoring unit electrically connected to said stimulation unit for monitoring the on-skin status of said electrode array;

an analysis unit for analyzing said on-skin status of said electrode array to determine the effective on-skin time of said electrode array; and a feedback unit for alerting the user when said analysis unit determines that the effective on-skin time exceeds a threshold.

In another preferred form of the present invention, there is provided a method for monitoring the on-skin time of a transcutaneous electrical nerve stimulation (TENS) device for providing TENS therapy to at least one nerve of a user through an electrode array, said method comprising the steps of:

applying the electrode array to the surface of the user's skin to provide electrical contact between the electrode array and the skin of the user;

electrically stimulating said at least one nerve of the user with an electrical stimulator connected to the electrode array;

monitoring the on-skin status of the electrode array;

analyzing the on-skin status of the electrode array to determine the effective on-skin time; and alerting the user of the effective on-skin time.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
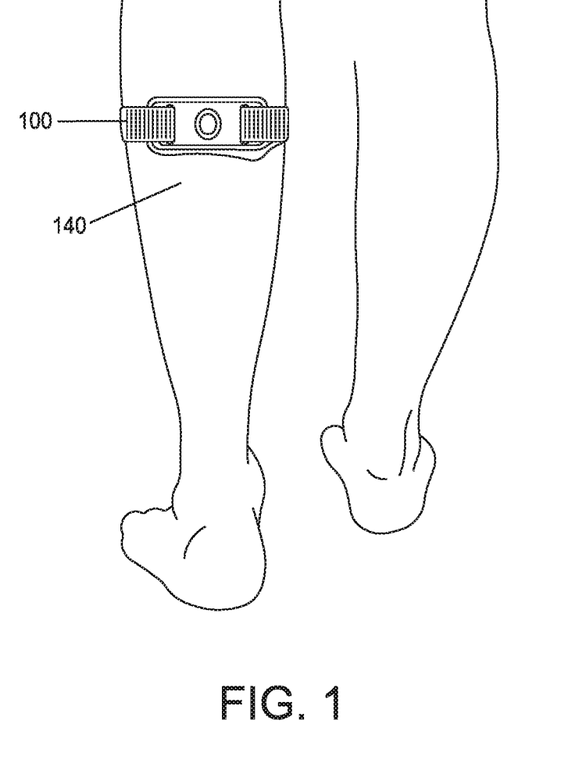
FIG. 1 is a schematic view showing a novel TENS device formed in accordance with the present invention, wherein the novel TENS device is mounted to the upper calf of a user.

FIG. 1 illustrates a novel TENS device 100 formed in accordance with the present invention, with the novel TENS device 100 being shown worn on a user's upper calf 140. A user may wear TENS device 100 on one or both legs (either one at a time or simultaneously).

Figure 2:
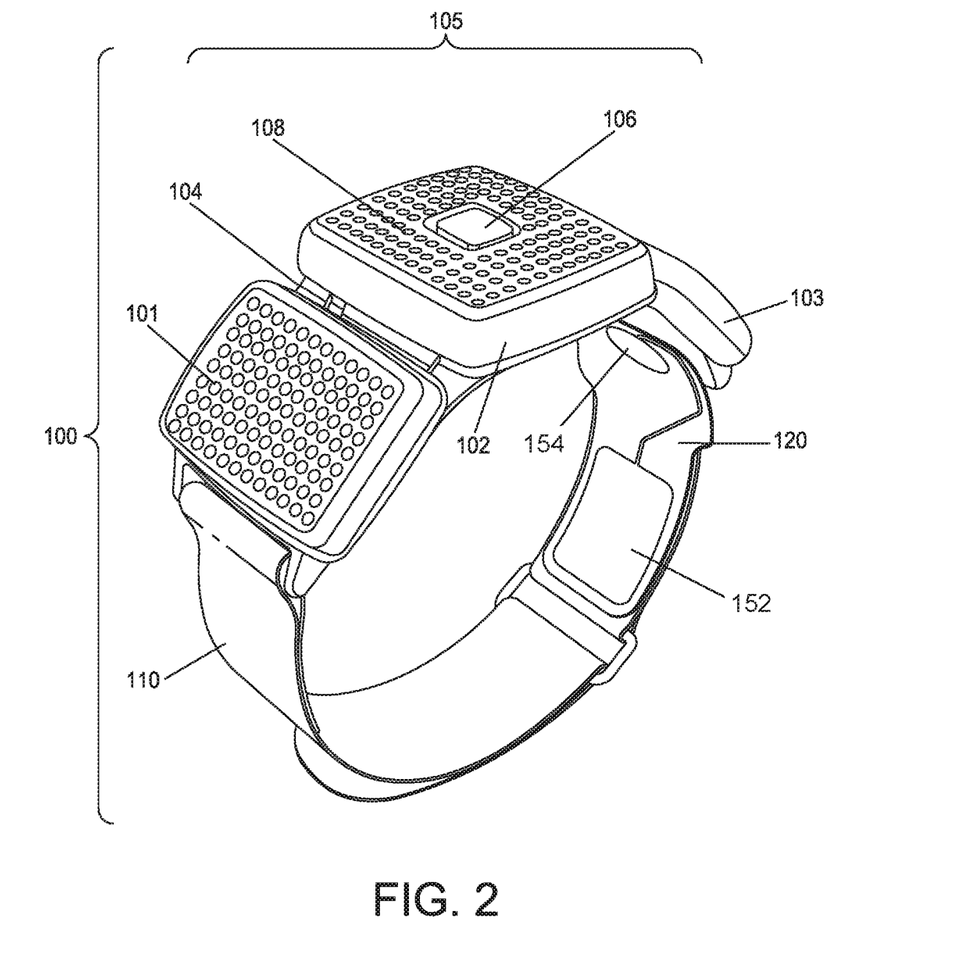
FIG. 2 is a schematic view showing the novel TENS device of FIG. 1 in greater detail.

TENS device 100 is shown in greater detail in FIG. 2 and preferably comprises three components: a stimulator 105, a strap 110, and an electrode array 120. Stimulator 105 preferably comprises multiple mechanically and electrically inter-connected compartments. In the exemplary TENS device 100 shown in FIG. 2, three compartments 101, 102, and 103 are shown. Compartments 101, 102, 103 are inter-connected by hinge mechanisms 104 (only one of which is visible in FIG. 2), thereby allowing TENS device 100 to conform to the curved anatomy of a user's leg. In a preferred embodiment, compartment 102 contains the TENS stimulation circuitry (hardware and software) and user interface elements 106 and 108. In a preferred embodiment, compartments 101 and 103 are smaller, auxiliary compartments that house a battery for powering the TENS stimulation circuitry and other ancillary elements, such as a wireless interface unit for allowing TENS device 100 to wirelessly communicate with other elements (e.g., a remote server, a smartphone, etc.). In another embodiment of the present invention, only one compartment 102 may be provided, in which case the single compartment 102 houses all of the TENS stimulation circuitry (hardware and software), battery and other ancillary elements, without the need for side compartments 101 and 103.

Still looking at FIG. 2, interface element 106 preferably comprises a push button for user control of electrical stimulation by TENS device 100, and interface element 108 preferably comprises an LED for indicating stimulation status and providing other feedback to the user. Additional user interface elements (e.g., an LCD display, audio feedback through a beeper or voice output, haptic devices such as a vibrating element, etc.) are also contemplated and are considered to be within the scope of the present invention.

The preferred embodiment of the invention is designed to be worn on the user's upper calf 140 as shown in FIG. 1 (although the TENS device could also be worn on other anatomical locations). TENS device 100, comprising stimulator 105, electrode array 120, and strap 110, is secured to upper calf 140 (or other anatomical location) by placing the apparatus in position and then tightening strap 110. More particularly, in one preferred form of the invention, electrode array 120 is deliberately sized and configured so that it will apply appropriate electrical stimulation to the appropriate anatomy of the user regardless of the specific rotational position of TENS device 100 on the leg (or other anatomical location) of the user. Although the preferred embodiment of the present invention comprises placement of the TENS device on the upper calf of the user, additional locations (such as above the knee, on an upper extremity, etc.) are also contemplated and are considered to be within the scope of the present invention. Furthermore, it is also contemplated that the TENS device may be placed on other anatomical locations of the user, e.g., the lower back of the user (however, it will be appreciated that in some of these alternative anatomical locations, electrode array 120 may not be able to supply appropriate electrical stimulation to the appropriate anatomy of the user regardless of the specific rotational position of the TENS device 100 on the anatomy of the user).

Figure 3:
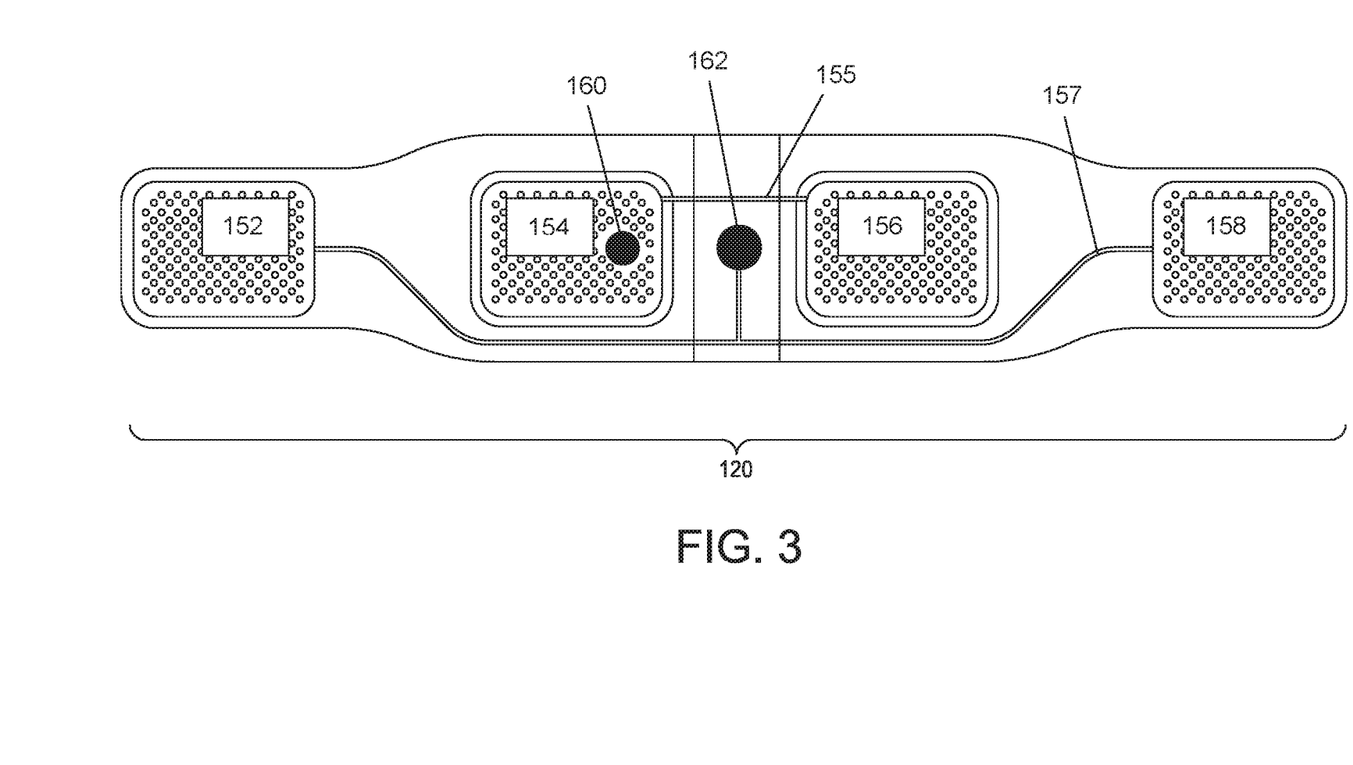
FIG. 3 is a schematic view showing the electrode array of the novel TENS device of FIG. 1 in greater detail.

FIG. 3 shows a schematic view of one preferred embodiment of electrode array 120. Electrode array 120 preferably comprises four discrete electrodes 152, 154, 156, 158, each having an equal or similar size (i.e., an equal or similar size surface area). Electrodes 152, 154, 156, 158 are preferably connected in pairs so that electrodes 154 and 156 (representing the cathode of TENS device 100) are electrically connected to one another (e.g., via connector 155), and so that electrodes 152 and 158 (representing the anode of TENS device 100) are electrically connected to one another (e.g., via connector 157). It should be appreciated that electrodes 152, 154, 156, 158 are preferably appropriately sized, and connected in pairs, so as to ensure adequate skin coverage regardless of the rotational position of TENS device 100 (and hence regardless of the rotational position of electrode array 120) on the leg (or other anatomical location) of a user. Furthermore, it should be appreciated that electrodes 152, 154, 156, 158 are not connected in an interleaved fashion, but rather are connected so that the two inside electrodes 154, 156 are connected to one another, and so that the two outside electrodes 152, 158 are connected to one another. This electrode connection pattern ensures that if the two outer electrodes 152, 158 should inadvertently come into contact with one another, an electrical short of the stimulation current flowing directly from cathode to anode will not occur (i.e., the electrode connection pattern ensures that the therapeutic TENS current is always directed through the tissue of the user).

Figure 4:
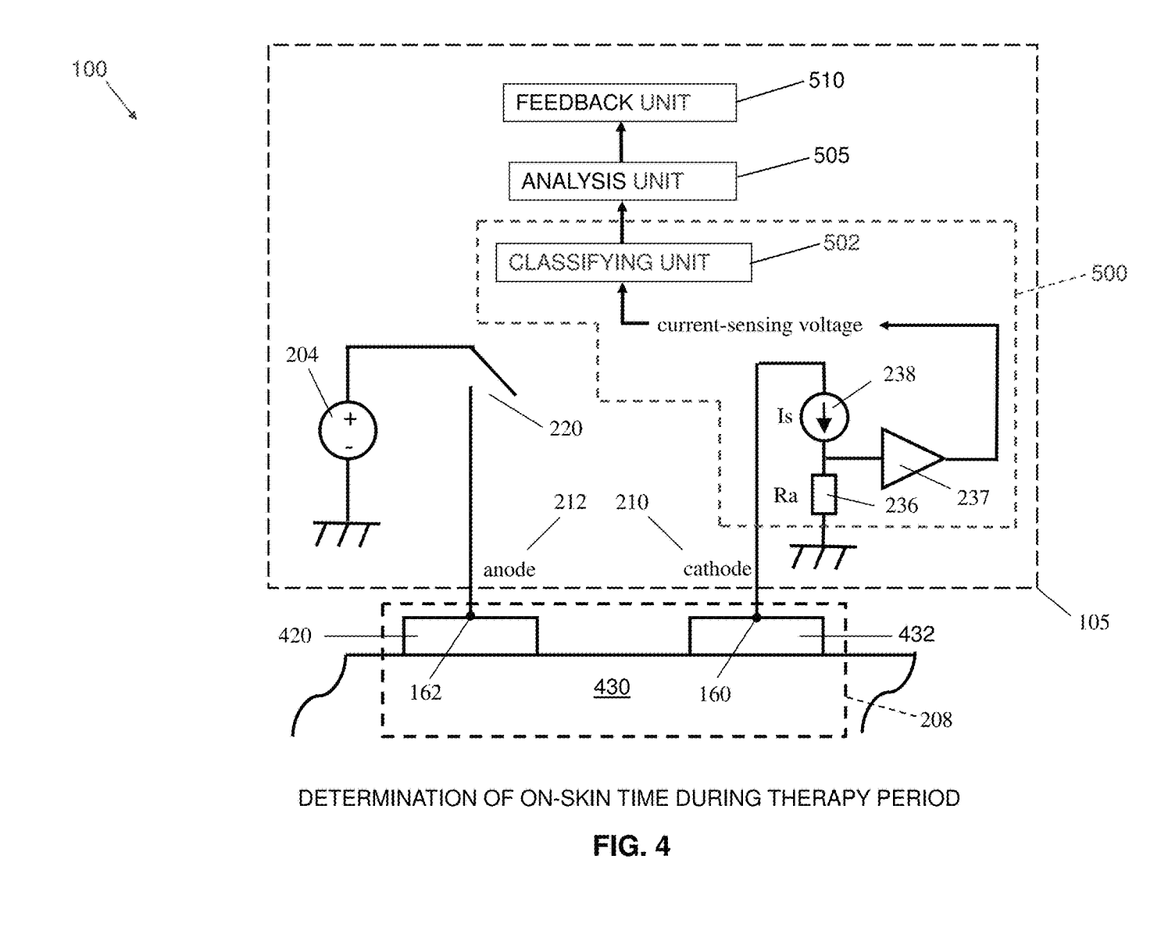
FIG. 4 is a schematic view showing apparatus for determining the on-skin time of the TENS device of FIG. 1 during a therapy period.
Figure 7:
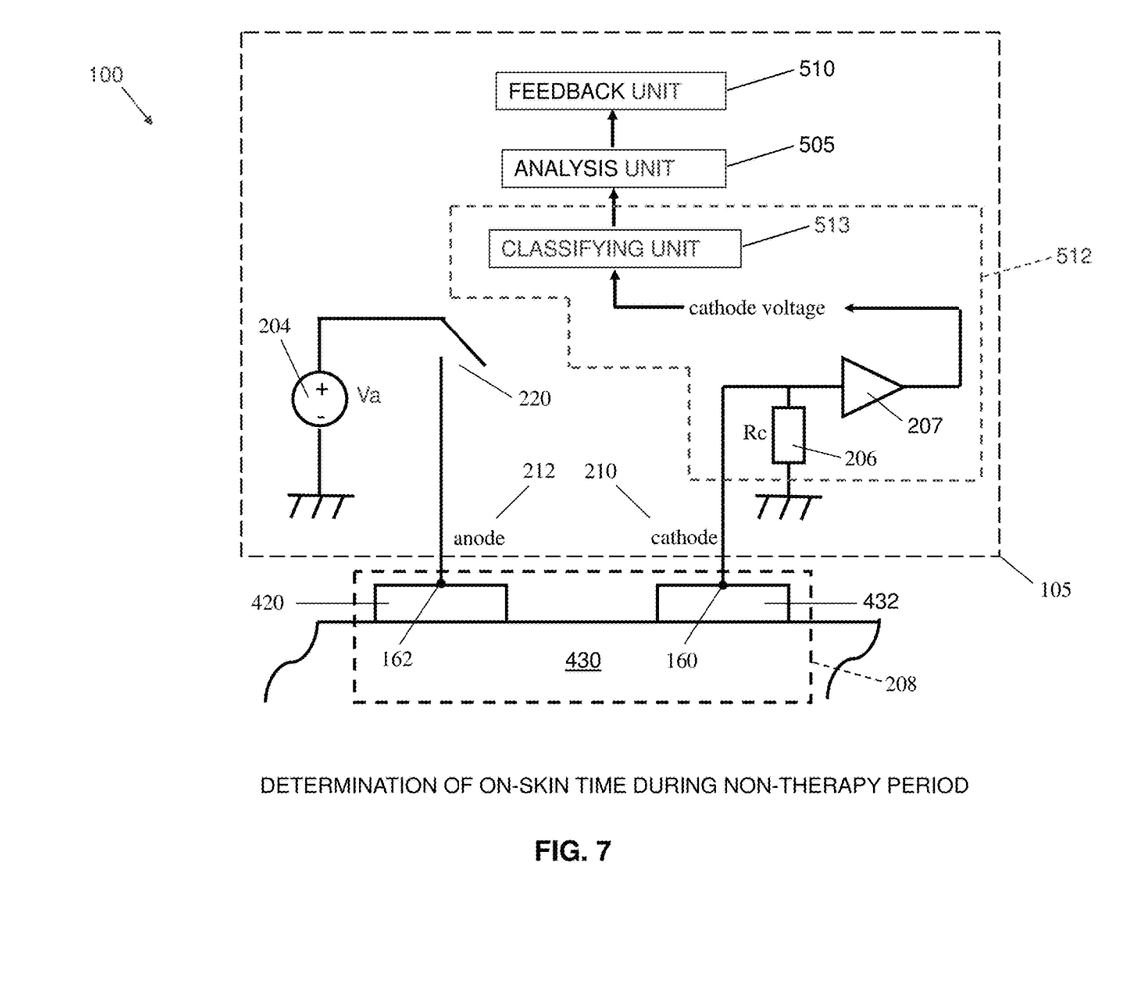
FIG. 7 is a schematic view showing apparatus for determining the on-skin time of the TENS device of FIG. 1 during a non-therapy period.

Electrical current (i.e., for therapeutic electrical stimulation to the tissue) is provided to the electrode pairs 154, 156 and 152, 158 by connectors 160, 162 which mate with complementary connectors 210, 212, respectively, on stimulator 105 (see FIGS. 4 and 7). Stimulator 105 generates electrical currents that are passed through electrodes 154, 156 and electrodes 152, 158 via connectors 160, 162, respectively.

In one preferred embodiment of the present invention, the skin-contacting conductive material of electrodes 152, 154, 156, 158 is a hydrogel material which is "built into" electrodes 152, 154, 156, 158. The function of the hydrogel material on the electrodes is to serve as an interface between the electrodes 152, 154, 156, 158 and the skin of the user (i.e., within, or adjacent to, or proximal to, the portion of the user's body in which the sensory nerves which are to be stimulated reside). Other types of electrodes such as dry electrodes and non-contact stimulation electrodes have also been contemplated and are considered to be within the scope of the present invention.

Further details regarding the construction and use of the various aspects of TENS device 100 are disclosed in (1) pending prior U.S. patent application Ser. No. 14/610,757, filed Jan. 30, 2015 by NeuroMetrix, Inc. and Shai N. Gozani et al. for APPARATUS AND METHOD FOR RELIEVING PAIN USING TRANSCUTANEOUS ELECTRICAL NERVE STIMULATION and the patent applications incorporated therein by reference; (2) pending prior U.S. patent application Ser. No. 14/230,648, filed Mar. 31, 2014 by Neurometrix, Inc. and Shai Gozani et al. for DETECTING CUTANEOUS ELECTRODE PEELING USING ELECTRODE-SKIN IMPEDANCE and the patent applications incorporated therein by reference; (3) pending prior U.S. patent application Ser. No. 14/253,628, filed Apr. 15, 2014 by Neurometrix, Inc. and Shai Gozani et al. for TRANSCUTANEOUS ELECTRICAL NERVE STIMULATOR WITH AUTOMATIC DETECTION OF USER SLEEP-WAKE STATE and the patent applications incorporated therein by reference; and (4) pending prior U.S. patent application Ser. No. 14/269,887, filed May 5, 2014 by NeuroMetrix, Inc. and Thomas Ferree et al. for TRANSCUTANEOUS ELECTRICAL NERVE STIMULATOR WITH USER GESTURE DETECTOR AND ELECTRODE-SKIN CONTACT DETECTOR, WITH TRANSIENT MOTION DETECTOR FOR INCREASING THE ACCURACY OF THE SAME and the patent applications incorporated therein by reference; all of which foregoing patent applications are hereby incorporated herein by reference.

Wearing the TENS device for an extended period of time without removing the TENS device from the contacted skin area may cause skin irritation for the user. It is therefore important to monitor the "on-skin" time duration of the TENS device and, where the "on-skin" time duration exceeds a limit, to provide the user with feedback and a reminder (prompt) to "air-out" the skin under the TENS device. By way of example but not limitation, this "airing-out" can be accomplished by removing the TENS device from the user's body altogether, or by repositioning the TENS device on the contralateral limb of the user, etc.

In view of the foregoing, the present invention comprises the provision and use of a novel TENS device which includes novel means to determine its on-skin time duration (e.g., the period of time over which the TENS device, including its electrodes, maintains constant, uninterrupted contact with the user's skin).

On-Skin Time During Therapy Period

During a period when the TENS device is providing active therapy to the user, current pulses with an intensity and duration optimized for therapeutic purposes are delivered to the user through the electrode-skin interface created by the electrodes placed on the skin and electrically connected to the stimulation circuitry of the TENS stimulator. During the therapy period, the presence or absence of electrode-skin contact (i.e., whether the TENS device is on-skin or off-skin) can be determined by measuring the stimulation current which is already flowing through the TENS device (i.e., so as to provide therapeutic nerve stimulation to the user).

Figure 5:
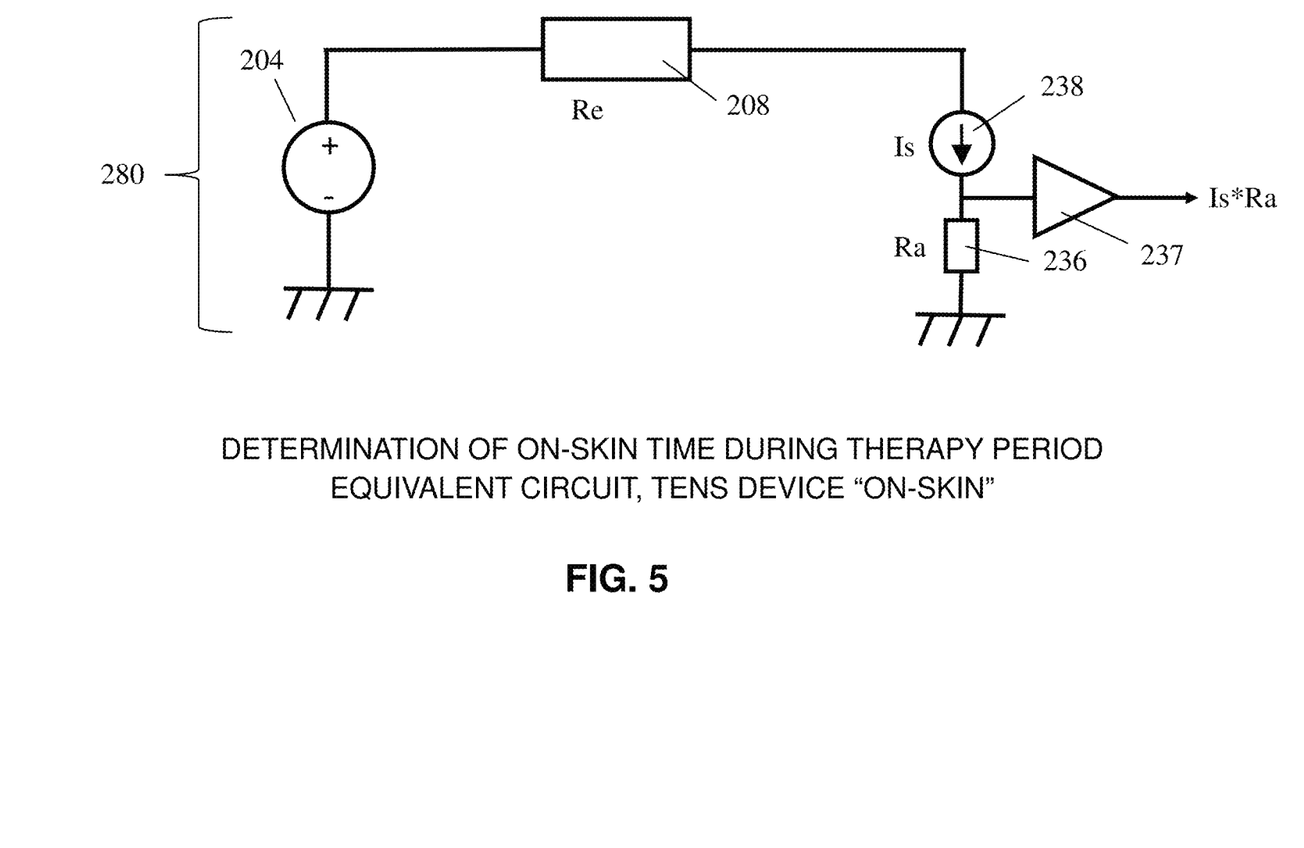
FIG. 5 is a schematic view showing the equivalent circuit for the apparatus of FIG. 4 during a therapy period and when the TENS device is on-skin.

More particularly, a preferred embodiment of the present invention is shown in FIG. 4. Stimulator 105 of TENS device 100 comprises a monitoring unit 500 which measures the stimulation current flowing through TENS device 100 so as to determine the occurrence of an on-skin condition. As seen in FIG. 4, monitoring unit 500 comprises a current source 238 which is programmed to deliver a stimulation current pulse Is (in one preferred form of the invention, Is=20 mA) when voltage source 204 is applied to the anode terminal 212 of TENS stimulator 105 by closing the switch 220. If the TENS device is being worn by the user, then user skin 430, interposed between anode electrode 420 (i.e., anode electrodes, 152, 158) and cathode electrode 432 (i.e., cathode electrodes 154, 156), will form an equivalent impedance 208 (i.e., Re), as shown in FIG. 5. The equivalent impedance 208 is also referred to as a stimulator load for the TENS device.

More particularly, when TENS device 100 is on the skin of the user, the equivalent circuit 280 shown in FIG. 5 approximates the real-world system of TENS device 100 and the body of the user. The current produced by current source 238 can then be sensed through the current sensing resistor 236 (e.g., Ra). The cathode voltage measured from the amplifier 237 will be non-zero and close to the target value of Is*Ra.

On the other hand, when the TENS device is not on the skin of the user, the equivalent circuit 290 (FIG. 6) represents the real-world system of TENS device 100 and the body of the user, and the current-sensing voltage measured from amplifier 237 will be zero.

Figure 6:
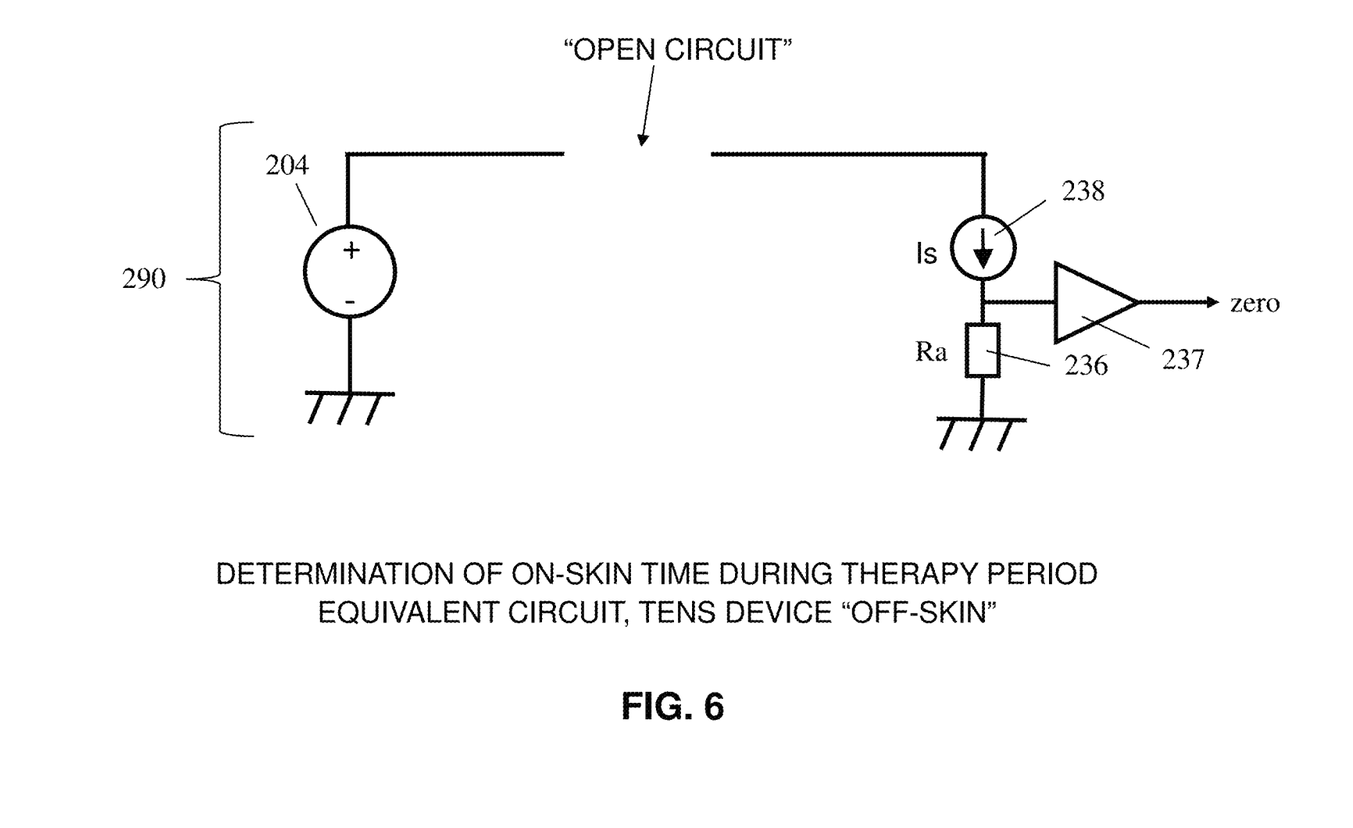
FIG. 6 is a schematic view showing the equivalent circuit for the apparatus of FIG. 4 during a therapy period and when the TENS device is off-skin.

If the stimulating current Is is of a reasonable magnitude and cannot be sensed (i.e., if the output of amplifier 237 is effectively zero), one may conclude that no electrode-skin contact is occurring (i.e., that the TENS device is "off-skin"). Otherwise, the TENS device is considered to be on-skin and classifying unit 502 of monitoring unit 500 will "set a flag" indicative of the on-skin condition. Analysis unit 505 reads the flags set by classifying unit 502 and, using this information, determines the on-skin time duration of the therapy periods. When the on-skin time duration meets a predetermined threshold, analysis unit 505 causes feedback unit 510 (e.g., a vibration module) to provide an appropriate alert to the user.

Thus, monitoring unit 500 comprises an appropriately-programmed circuit module which identifies when the current sensing voltage output by amplifier 237 indicates the presence of an on-skin condition for TENS device 100. The construction of the appropriately-programmed circuit module of monitoring unit 500 will be apparent to those skilled in the art in view of the present disclosure.

And classifying unit 502 comprises an appropriately-programmed circuit module which "sets a flag" indicative of the on-skin condition for TENS device 100. The construction of the appropriately-programmed circuit module of classifying unit 502 will be apparent to those skilled in the art in view of the present disclosure.

And analysis unit 505 comprises an appropriately-programmed circuit module which monitors the flags set by classifying unit 502 and determines the on-skin time duration for TENS device 100 during the therapy periods and, when the on-skin time meets a predetermined threshold, sends an alert instruction to feedback unit 510. The construction of the appropriately-programmed circuit module of analysis unit 505 will be apparent to those skilled in the art in view of the present disclosure.

And feedback unit 510 comprises an appropriately-programmed circuit module which, when it receives the alert instruction from analysis unit 505, appropriately alerts the user. The construction of the appropriately-programmed circuit module of feedback unit 510 will be apparent to those skilled in the art in view of the present disclosure.

On-Skin Time During Non-Therapy Period

Novel TENS device 100 is also provided with means to measure electrode-skin contact time when the TENS device is not actively providing TENS stimulation to the user, i.e., by providing means for monitoring the device's on-skin status during a non-therapy period. The ability to monitor the device's on-skin status under non-stimulation conditions is important, inasmuch as a user may wear the TENS device for a much longer period of time than the total stimulation time, which can result in excessive on-skin time.

A preferred embodiment of the present invention is shown in FIG. 7. Stimulator 105 of TENS device 100 also comprises a monitoring unit 512 which measures the cathode voltage of TENS device 100 so as to determine the occurrence of an on-skin condition. As seen in FIG. 7, in this form of the invention, when TENS device 100 is in its non-therapy mode, a voltage of 20 volts from voltage source 204 is applied to the anode terminal 212 of TENS stimulator 105 by closing the switch 220. If the TENS device is worn by the user, then user skin 430, interposed between anode electrode 420 (i.e., anode electrodes, 152, 158) and cathode electrode 432 (i.e., cathode electrodes 154, 156), will form an equivalent impedance 208 in a voltage divider circuit. The equivalent impedance 208 is also referred to as a stimulator load of the TENS device.

Figure 8:
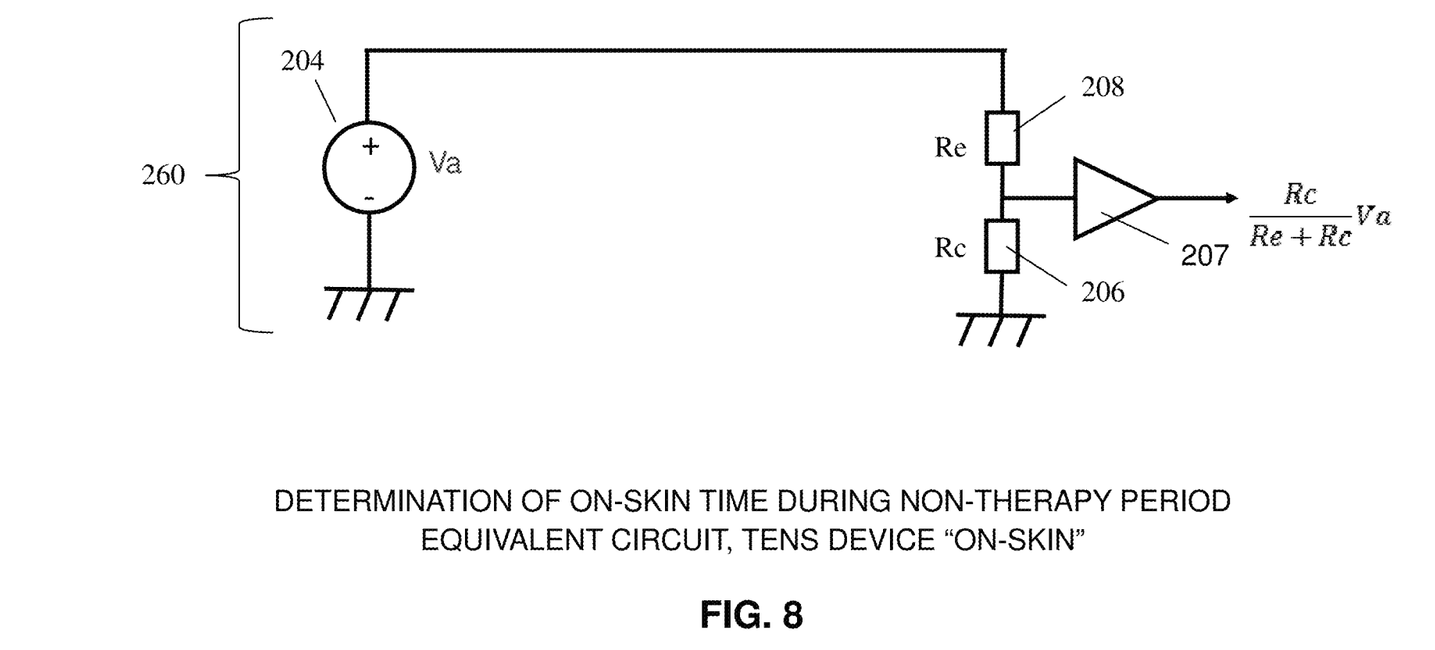
FIG. 8 is a schematic view showing the equivalent circuit for the apparatus of FIG. 7 during a non-therapy period and when the TENS device is on-skin.

More particularly, when TENS device 100 is on the skin of the user, the equivalent circuit 260 shown in FIG. 8 represents the real-world system of TENS device 100 and the body of the user, and the anode voltage (e.g., voltage Va of voltage source 204) can be sensed through the voltage divider impedances 206 (i.e., Rc) and 208 (i.e., Re). The cathode voltage measured from the amplifier 207 will be non-zero and close to the anode voltage Va of voltage source 204 when voltage divider Rc (206) is chosen such that Rc is much larger than the expected electrode-skin impedance Re. By way of example but not limitation, in one preferred form of the invention, Rc is chosen to have a value of 1,000,000 ohms when Re is expected to have a value of 100,000 ohms.

On the other hand, when TENS device 100 is not on the skin of the user, the equivalent circuit 270 (FIG. 9) represents the real-world system of TENS device 100 and the body of the user, and the cathode voltage from amplifier 207 will be zero.

Figure 9:
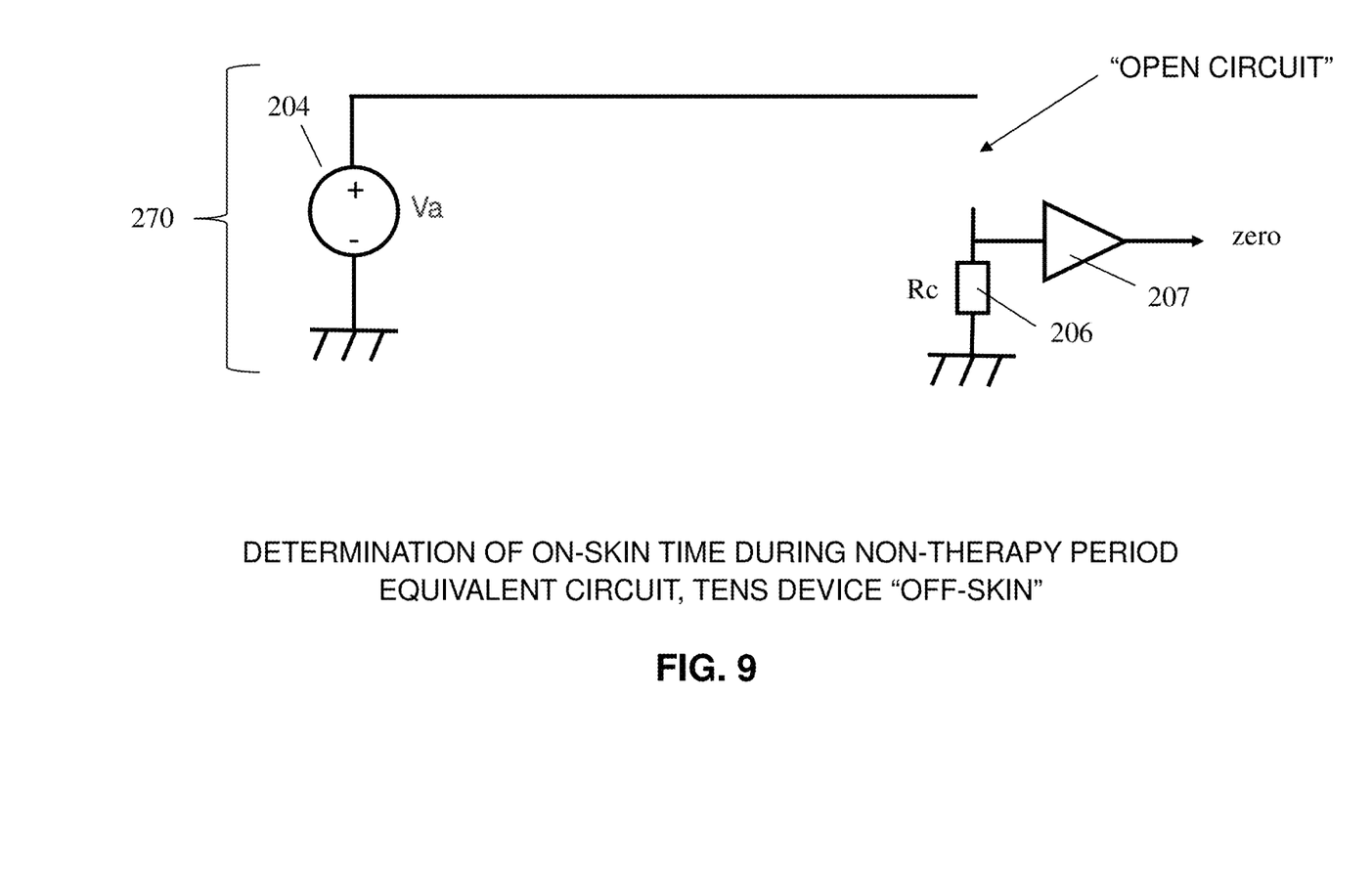
FIG. 9 is a schematic view showing the equivalent circuit for the apparatus of FIG. 7 during a non-therapy period and when the TENS device is off-skin.

Thus, where the cathode voltage measured from the amplifier 207 is non-zero and close to the anode voltage Va of voltage source 204, one may conclude that electrode-skin contact is occurring (i.e., that TENS device 100 is "on-skin"), and classifying unit 513 of monitoring unit 512 will "set a flag" indicative of the on-skin condition. Analysis unit 505 reads the flags set by classifying unit 513 and, using this information, determines the on-skin time duration of TENS device 100 during non-therapy periods. When the on-skin time meets a predetermined threshold, analysis unit 505 causes feedback unit 510 (e.g., a vibration module) to provide an appropriate alert to the user.

Thus, monitoring unit 512 comprises an appropriately-programmed circuit module which identifies when the cathode voltage output by amplifier 207 indicates the presence of an on-skin condition. The construction of the appropriately-programmed circuit module of monitoring unit 512 will be apparent to those skilled in the art in view of the present disclosure.

And classifying unit 513 comprises an appropriately-programmed circuit module which "sets a flag" indicative of the on-skin condition for TENS device 100. The construction of the appropriately-programmed circuit module of classifying unit 513 will be apparent to those skilled in the art in view of the present disclosure.

And analysis unit 505 comprises an appropriately-programmed circuit module which monitors the flags set by classifying unit 513 and determines the on-skin time duration for TENS device 100 during the non-therapy periods and, when the on-skin time meets a predetermined threshold, sends an alert instruction to feedback unit 510. The construction of the appropriately-programmed circuit module of analysis unit 505 will be apparent to those skilled in the art in view of the present disclosure.

And feedback unit 510 comprises an appropriately-programmed circuit module which, when it receives the alert instruction from analysis unit 505, appropriately alerts the user. The construction of the appropriately-programmed circuit module of feedback unit 510 will be apparent to those skilled in the art in view of the present disclosure.

Use of Two Different Cathode-Side Detection Circuits to Identify the On-Skin Time of the TENS Device, Depending on Whether the TENS Device is in Therapy Mode or Non-Therapy Mode Thus it will be seen that TENS device 100 comprises two different cathode-side detection circuits (i.e., monitoring unit 500, including its classifying unit 502; and monitoring unit 512, including its classifying unit 513) to identify the on-skin status of the TENS device, depending on whether the TENS device is in its therapy mode or its non-therapy mode.

More particularly, when TENS device 100 is in its therapy mode, the cathode side detection circuit shown in FIG. 4 (i.e., monitoring unit 500, including classifying unit 502) may be used to detect the on-skin/off-skin condition of TENS device 100, with the equivalent circuit 280 of FIG. 5 representing the "on-skin" condition and with the equivalent circuit 290 of FIG. 6 representing the "off-skin" condition.

Furthermore, it will be appreciated that when TENS device 100 is in its non-therapy mode, the cathode side detection circuit shown in FIG. 7 (i.e., monitoring unit 512, including classifying unit 513) may be used to detect the on-skin/off-skin condition of TENS device 100, with the equivalent circuit 260 of FIG. 8 representing the "on-skin" condition and with the equivalent circuit 270 of FIG. 9 representing the "off-skin" condition.

It will be appreciated that TENS device 100 preferably includes automatic selection circuitry for determining whether the output of the cathode side detection circuit of FIG. 4 (i.e., monitoring unit 500, including classifying unit 502), or whether the output of the cathode side detection circuit of FIG. 7 (i.e., monitoring unit 512, including classifying unit 513), is to be used to determine the on-skin/off-skin condition of TENS device 100. In other words, TENS device 100 preferably includes circuitry which automatically uses the cathode side detection circuit of FIG. 4 (i.e., monitoring unit 500, including classifying unit 502) to determine the on-skin/off-skin condition of TENS device 100 when TENS device 100 is in its therapy mode, and the cathode side detection circuit of FIG. 7 (i.e., monitoring unit 512, including classifying unit 513) to determine the on-skin/off-skin condition of TENS device 100 when TENS device 100 is in its non-therapy mode.

It will also be appreciated that analysis unit 505 of TENS device 100 is configured to use an aggregation of the outputs of monitoring unit 500 (including classifying unit 502) and monitoring unit 512 (including classifying unit 513) to determine the on-skin time duration of the TENS device, since TENS device 100 may be worn continuously across various therapy and non-therapy time periods. In other words, it is important that analysis unit 505 be reading the on-skin flags of both classifying unit 502 and classifying unit 513 so as to obtain an accurate measure of the total on-skin time duration of the TENS device.

Furthermore, it should be appreciated that analysis unit 505 may be configured to use various measures to identify a threshold on-skin time duration, e.g., analysis unit 505 may be configured to send an alert instruction to feedback unit 510 when the total constant, uninterrupted-contact on-skin time exceeds a predetermined number (e.g., when the total constant, uninterrupted-contact on-skin time exceeds 4 hours), or analysis unit 505 may be configured to send an alert instruction to feedback unit 510 when the total on-skin time within a given time period exceeds a predetermined number (e.g., when analysis unit 505 detects 8 hours of on-skin time within a time period of 10 hours), etc.

Again, analysis unit 505 comprises an appropriately-programmed circuit module configured to use an appropriate measure to identify a threshold on-skin time duration. The construction of the appropriately-programmed circuit module of analysis unit 505 will be apparent to those skilled in the art in view of the present disclosure.

Alerting the User when the On-Skin Time of a Transcutaneous Electrical Nerve Stimulator (TENS) Device Exceeds a Threshold To maintain a healthy skin condition, it is important for the skin area under the TENS device to be re-exposed to open air after a total on-skin time duration of the TENS device exceeds a threshold.

In one form of the present invention, TENS device 100 is configured so that when analysis unit 505 determines that the total on-skin time of the TENS device exceeds a threshold, the TENS device then provides feedback and a reminder (prompt) to the user using feedback unit 510, e.g., through electro-tactile feedback or other means.

The total on-skin time duration threshold can be set by the device manufacturer with a default value. The total on-skin time duration threshold can also be set by the user or by the recommendation of a healthcare provider based on the condition of the user (e.g., skin condition, age, gender, etc.). The total on-skin time duration threshold may also be different for daytime use and for nighttime use.

In another form of the present invention, analysis unit 505 of the TENS device is configured so that the "effective" on-skin time duration is used to determine when the TENS device should activate the reminder for the user (instead of using the "total on-skin time duration" to trigger the reminder for the user). Effective on-skin time can be just the total accumulated time in which the TENS device has been on-skin, either during a therapy period, a non-therapy period, or a combination of therapy and non-therapy periods. The effective on-skin time calculation can also assign a different (higher) weight to the time period in which stimulation is on-going during therapy in order to take into consideration an additional skin irritation effect caused by the TENS stimulating current. Further, the weight factor during the stimulation time period can be made to be proportional to the stimulation intensity. The effective on-skin time calculation can also use electrode-skin impedance as a weight factor to the time period in which the impedance is measured to account for various electrode-skin contact conditions, as well as adverse changes in skin conditions that are reflected in the impedance (such as a change in the electrode-skin capacitance due to inflammation).

The feedback to the user provided by feedback unit 510 can be the delivery of a sequence of electric stimulation pulses with a distinct pattern so that it will be recognized by the user as a signal to "air-out" the skin under the device. The pulse train can have a constant intensity or variable intensities with the aim to attract the user's attention. The feedback can be haptic perception via mechanical vibrations. The feedback can be disabled at night when the device determines that the user is asleep in order to avoid waking the user. The feedback can also be presented to an external device such as an application running on a nearby smartphone (preferably a smartphone which has been authenticated for secure communications with TENS device 100). Another means of feedback can be an alert to a caregiver of the user (e.g., via text message) if the user is unable to initiate the device removal action on his or her own.

The effective device on-skin time can also be used as a part of metrics to determine the TENS utilization profile of a given user. For example, the percentage of the on-skin time that is devoted to actual TENS stimulation may be indicative of the severity of the pain of the user, based on the assumption that the user would initiate a pain-relieving TENS stimulation session more often if the severity of the pain is higher.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for monitoring the on-skin time of a transcutaneous electrical nerve stimulation (TENS) device, said method comprising the steps of:
   applying an electrode array to the skin of the user to provide contact between the electrode array and the skin of the user;
   electrically stimulating at least one nerve of the user with an electrical stimulator connected to the electrode array;
   monitoring the electrode array to determine if the electrode array is positioned on the skin of the user and, when the electrode array is positioned on the skin of the user, recording that determination as an on-skin condition, wherein monitoring the electrode array to determine if the electrode array is positioned on the skin of the user includes monitoring the electrode array when electrical stimulation is being delivered to the user and when electrical stimulation is not being delivered to the user;
   calculating a duration of time of the on-skin condition; and
   providing the user with feedback of the duration of time of the on-skin condition.

2. A method according to claim 1 wherein monitoring said electrode array is accomplished with the same electrical stimulation as that used to stimulate the at least one nerve of the user.

3. A method according to claim 1 wherein monitoring said electrode array is accomplished with electrical stimulation different from that used to stimulate the at least one nerve of the user.

4. A method according to claim 3 wherein monitoring said electrode array is accomplished with electrical stimulation pulses having a constant current intensity level.

5. A method according to claim 3 wherein monitoring said electrode array is accomplished with electrical stimulation pulses having a constant voltage intensity level.

6. A method according to claim 1 wherein monitoring said electrode array is accomplished with electrical stimulation having an intensity level providing therapeutic benefit to the user.

7. A method according to claim 1 wherein monitoring said electrode array is accomplished with electrical stimulation having an intensity below the electrotactile sensation threshold of the user.

8. A method according to claim 1 wherein monitoring said electrode array is determined by comparing a target stimulation intensity level with an actual stimulation intensity level delivered by the electrical stimulator through said electrode array to the user.

9. A method according to claim 1 wherein monitoring said electrode array to determine if the electrode array is positioned on the skin of the user is determined by comparing a target threshold value with an actual voltage-divider output when the electrical stimulation is a constant voltage source applied to an input of the voltage-divider.

10. A method according to claim 9 wherein the voltage-divider output is a voltage drop across an electronic component.

11. A method according to claim 10 wherein the voltage-divider input is applied to said electronic component and a stimulator load, wherein the stimulator load is the electrode-skin interface created by said electrode array placed on the skin of the user and connected to said electrical stimulator.

12. A method according to claim 1 wherein the duration of time of the on-skin condition is a total sum of consecutive time intervals during which the electrode array is positioned on the skin of the user.

13. A method according to claim 1 wherein the duration of time of the on-skin condition is calculated as an effective on-skin time duration, wherein the effective on-skin time duration is a total sum of weighted consecutive time intervals during which said electrode array is determined to be of on-skin condition.

14. A method according to claim 13 wherein the weight factor for each time interval is a function of current intensity passing through the stimulator load during that time interval.

15. A method according to claim 13 wherein the weight factor for each time interval is a function of measured impedance value of the stimulator load for that time interval.

16. A method according to claim 1 wherein the user is provided with feedback with a display of the duration of time of the on-skin condition.

17. A method according to claim 1 wherein the user is provided with feedback only when the duration of time of the on-skin condition exceeds a threshold.

18. A method according to claim 17 wherein the feedback is a sequence of electrical stimulation pulses delivered to the user.

19. A method according to claim 17 wherein the feedback is a sequence of mechanical vibration pulses delivered to the user.

20. A method according to claim 17 wherein the feedback is provided by a notification to a separate, authenticated device.

21. A method according to claim 20 wherein said device comprises a smartphone connected with to the TENS device via a wireless communication protocol.

22. A method according to claim 1 wherein the duration of time of the on-skin condition is a total sum of consecutive time intervals during which the electrode array is positioned on the skin of the user within a time period.

23. A method according to claim 22 wherein said time period is a calendar day.

24. A method according to claim 22 wherein said time period is a rolling 24-hour time window.

25. A method according to claim 17 wherein said threshold is a function of skin conditions of the user.

26. A method according to claim 1 wherein said feedback is a display of a utilization profile of TENS therapy according to the duration of the on-skin condition.

27. A method for monitoring the on-skin time of a transcutaneous electrical nerve stimulation (TENS) device, said method comprising the steps of:
creating a profile of a user;
applying an electrode array to the skin of the user to provide contact between the electrode array and the skin of the user;
electrically stimulating at least one nerve of the user with an electrical stimulator connected to the electrode array;
monitoring the electrode array to determine if the electrode array is positioned on the skin of the user and, when the electrode array is positioned on the skin of the user, recording that determination as an on-skin condition, wherein monitoring the electrode array to determine if the electrode array is positioned on the skin of the user includes monitoring the electrode array when electrical stimulation is being delivered to the user and when electrical stimulation is not being delivered to the user;
calculating a duration of time of the on-skin condition; and
providing the user with feedback of the duration of time of the on-skin condition, wherein the feedback depends upon the profile of the user.

28. A method according to claim 27 wherein said profile comprises demographic characteristics of the user.

29. A method according to claim 27 wherein said profile comprises at least one health condition of the user.

30. A method according to claim 29 wherein the health condition comprises at least one skin condition of the user.

31. A method according to claim 30 wherein said skin condition comprises at least one from the group consisting of dry skin, sensitive skin, and normal skin.

* * * * *